United States Patent [19]

Straumann et al.

[11] 4,180,910
[45] Jan. 1, 1980

[54] IMPLANT FOR AN ARTIFICIAL TOOTH

[75] Inventors: Fritz Straumann, Waldenburg; Franz Sutter, Niederdorf, both of Switzerland

[73] Assignee: Institut Straumann AG, Switzerland

[21] Appl. No.: 951,242

[22] Filed: Oct. 13, 1978

[30] Foreign Application Priority Data

Oct. 31, 1977 [CH] Switzerland ............ 13203/77

[51] Int. Cl.² .................................. A61C 13/00
[52] U.S. Cl. .................................. 433/173; 433/201
[58] Field of Search .................................. 32/10 A

[56] References Cited

U.S. PATENT DOCUMENTS 3,499,222  3/1970  Linkow et al. .............. 32/10 A
3,829,972  8/1974  Pasquzlini .............. 32/10 A Primary Examiner—Robert Peshock
Attorney, Agent, or Firm—McGlew and Tuttle

[57] ABSTRACT

An implant for fixing an artificial replacement tooth to a jaw bone comprises a post for firmly holding the replacement tooth and at least two hollow cylindrical bodies. The bodies have mutually parallel axes, are rigidly connected to the post and open at one axial end. The cylindrical wall of each body is intended to be inserted into the jaw bone and is provided with means defining passages through which the jaw bone can grow to secure the implant to the jaw. A group of teeth may be fixed to the jaw by the use of a bridge and two or more implants.

17 Claims, 12 Drawing Figures

IMPLANT FOR AN ARTIFICIAL TOOTH

BACKGROUND OF THE INVENTION

The present invention relates to an implant for fixing an artificial remplacement tooth to a jaw.

An implant for fixing an artificial remplacement tooth is disclosed in U.S. Pat. No. 3,499,222. This implant comprises a hollow cylindrical body open at one end and intended for anchoring the implant in the jaw. At its other end, the hollow cylinder is closed by a conical end wall. A cylindrical post coaxial with the hollow cylinder is connected to this wall at its centre. The cylindrical portion of the wall of the hollow cylindrical body is provided with passages therethrough.

In this known implant, the length of the cylindrical body measured from the end wall is more than twice as large as the diameter of the body. For adequate anchorage to be obtained with such a slender body, the body would need to be relatively long. Since, however, the implant must not penetrate into the nerve duct of the jaw, the body cannot be made as long as might be desired. If a so-called bridge, that is a remplacement comprising an entire group of artificial teeth, is to be fixed by two of these known implants, it is almost impossible to obtain a sufficiently firm anchorage. This is especially so when the jaw has already reformed, due to the natural teeth having been missing for a fairly long period.

The conical end wall of the known implants is limited from the hollow cylindrical body and from the post by sharp edges. Furtheron, the conical end wall is completely closed. It has been found that these features of the known implant are likely to induce inflammations and resorption of the bone.

An object of the present invention is to provide an implant, which enables an artificial tooth or group of teeth to be firmly anchored by means of one implant or an implant at each end of the group.

Another object of the invention is to provide an implant avoiding inflammations and bone resorption.

SUMMARY OF THE INVENTION

According to the present invention there is provided an implant for fixing an artificial replacement tooth to a jaw, comprising a post for firmly holding said replacement tooth and at least two hollow cylindrical bodies having parallel axes, said bodies each being rigidly connected to said post, open at a respective one axial end and having a cylindrical wall which is intended to be inserted into the bone of said jaw and which is provided with means defining passages therethrough.

BRIEF DESCRIPTION OF DRAWINGS

Embodiments of the present invention will now be more particularly described by way of example and with reference to the accompanying drawings in which.

DESCRIPTION OF THE PREFERRED EMBODIMENTS

Figure 1:
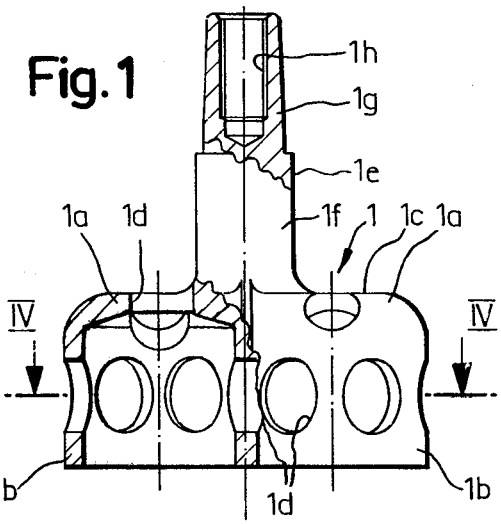
FIG. 1 shows an elevation on a wide face of a partially cutaway implant comprising two hollow cylindrical bodies, the cylindrical walls of which are directly and integrally connected together.
Figure 2:
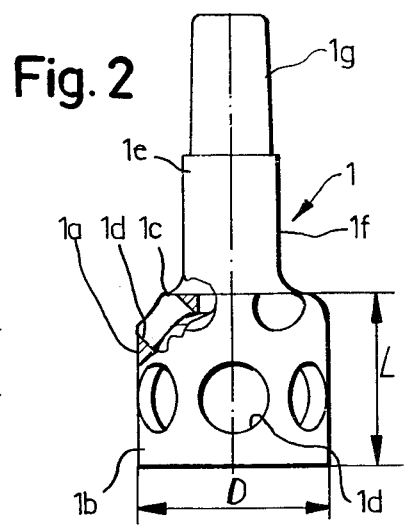
FIG. 2 shows a view on a narrow face of the partly cutaway implant shown in FIG. 1.
Figure 3:
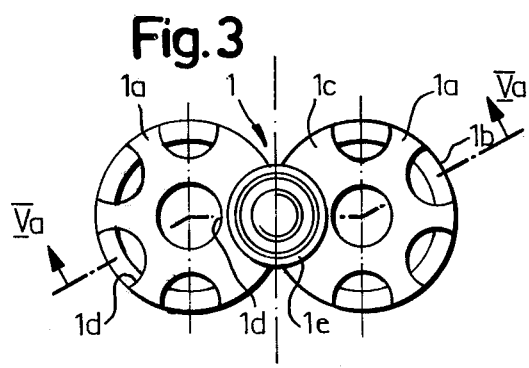
FIG. 3 shows a plan view of the implant.
Figure 4:
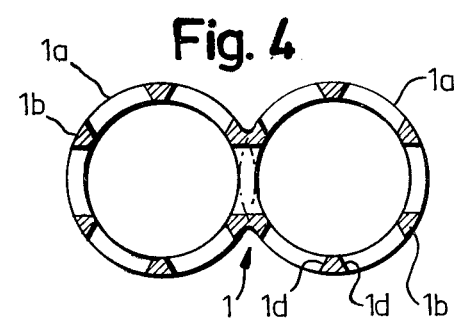
FIG. 4 shows a section along IV—IV of FIG. 1.
Figure 5:
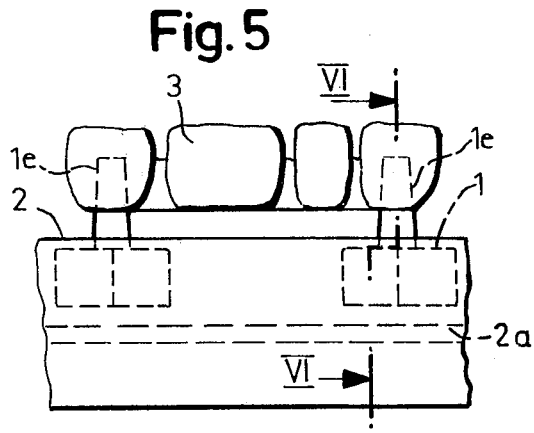
FIG. 5 shows an elevation of an alveolar bone with two inserted implants which carry a bridge, the soft tissue being omitted.

The implant shown in FIGS. 1 to 4 comprises two hollow cylindrical bodies 1a with mutually parallel axes. The bodies 1a have circular cylindrical walls 1b which join each other integrally, so that the external surface of the walls 1b continue into each other and the notional continuations of the external surfaces shown in dot-and-dash line in FIG. 4 would intersect each other. The hollow bodies 1a are each open at one end (the lower end in the drawing) and have at the other end an end wall 1c, which joins the wall 1b with a rounded portion. Both the cylindrical wall 1b and the end wall 1c have passages 1d, which are formed by bores and are more or less uniformly distributed over the two walls. There is a hole 1d at the centre of each end wall 1c. The other holes 1d are disposed along two arcs concentric to the bodies axis, the sector angle between two successive holes being 60°. The one, upper pitch circle of the holes is situated in the transition region between the two walls 1b, 1c, and the other, lower pitch circle in the region of the wall 1b. In the upper pitch circle, a hole is absent where the hollow bodies join together. In the lower pitch circle, the two hollow bodies 1a have one hole in common, which therefore connects together the internal spaces of the two hollow bodies 1a. The implant also comprises a post 1e, situated centrally between the axes of the two hollow bodies and having its axis parallel to those of the hollow bodies. The post 1e has a cylindrical portion 1f, connected by a rounded fillet with the two end walls 1c. The cylindrical portion 1f is followed by a somewhat more slender end portion 1g, which tapers towards a free end. The post 1e is provided with a blind threaded bore 1h, penetrating coaxially into the post from its free end.

The implant 1 is made of metal and from an integral, i.e., a single member. The member comprises compact, i.e., non-porous titanium. When the member has the form shown in FIGS. 1 to 4 and in particular is provided with all the trough bores, a thin coating of titanium granules is applied to it by flame spraying, these granules fusing partly together and to the member. In this manner, a rough surface is produced comprising pores, most of which have a diameter of 1 to 10 μm, although still smaller pores are also present. The porous layer is sprayed at least onto the external surfaces of the cylindrical wall 1b and preferably also onto the external surface of the end wall 1c, the internal surfaces of all the walls and the boundary surfaces of the holes. The length L of the cylinders measured from the outer face of the closure wall 1c, is preferably from about 4 to 6 mm. The external diameter D of the hollow cylinders 1a is preferably from 0.75 to 1.25 times the length L. In the embodiment shown in FIGS. 1 to 4, the length L is smaller than the diameter D and is about 90% of the latter. The total material thickness of the walls 1b, 1c is about 10% of the diameter D. The thickness of the sprayed-on titanium coating is about 10% of the total material thickness 1b, 1c of the walls.

Figure 5A:
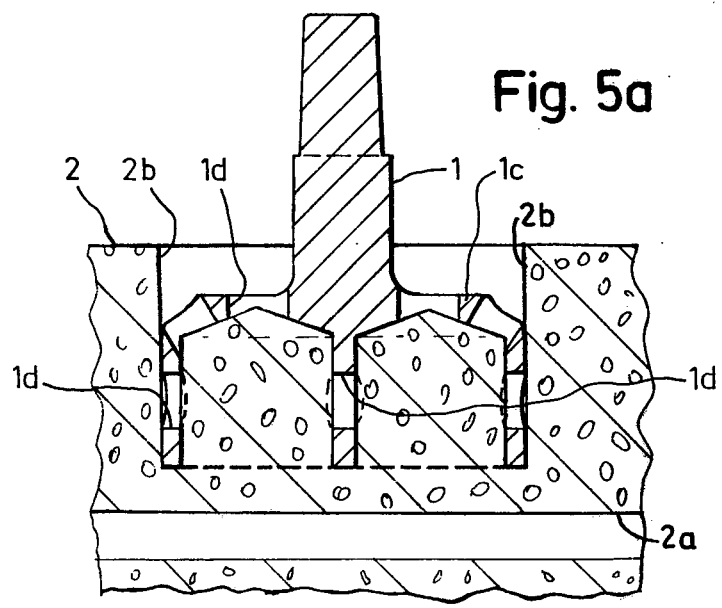
FIG. 5a shows a section of one of the implants inserted in the alveolar bone, immediately after the insertion of the implant, the soft tissues being omitted and the section being taken along line Va—Va of FIG. 3.

An explanation will now be given, with reference to FIGS. 5, 5a, 5b and 6, of how a synthetic tooth replacement can be fixed to the lower jaw by means of two implants 1. In FIGS. 5, 5a, 5b and 6, reference 2 designates the alveolar bone and 2a its nerve duct. In order to fix each implant 1, an opening 2b shown in FIG. 5a is drilled, for each hollow body, in the alveolar bone. This opening 2b comprises, in its upper part, a bore to receive the end wall 1c and, in its lower part, an annular groove to receive the cylindrical wall 1b. The diameters of the openings are so designed that the implants can be pressed in and are then firmly seated. The outer diameter of the cylindrical walls 1b may for instance be 0.05 to 0.1 mm greater than the outer diameter of the annular grooves. The studs of bone remaining inside the groove are approximately complementary to the inner space of the hollow cylindrical bodies 1a. Therefore, only a small amount of bone material is taken away and each implant 1 is relatively firmly fixed immediately after its insertion. The depths of the openings are so dimensioned that the openings do not intersect the nerve duct 2a, and that the end walls 1c of the inserted implant are situated about 1 mm below the crest of the bone. The end of the shaft portion 1f which is integral with the hollow body is therefore than also situated in the region of the alveolar bone 2. The remaining part of the cylindrical post 1f and the conical end portion 1g project above the alveolar bone. A group of synthetic teeth, a so-called bridge, is then seated as replacement teeth 3 on the posts 1e of the implants. The bridge, shown simplified here, rests upon the shoulders present at the transition between the cylindrical portion 1f and the end portion 1g of the post 1e and can be fixed to each post 1e by a screw 5.

Figure 6:
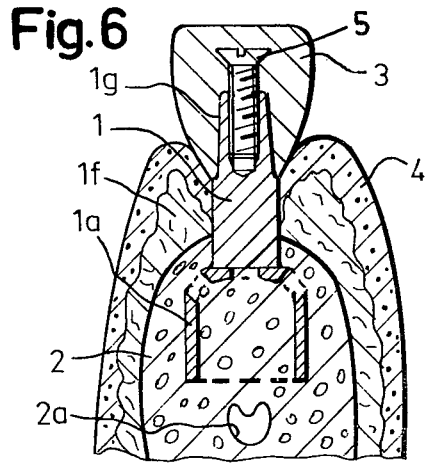
FIG. 6 shows a section along VI—VI of FIG. 5 to a larger scale and illustrating the soft tissues.
Figure 5B:
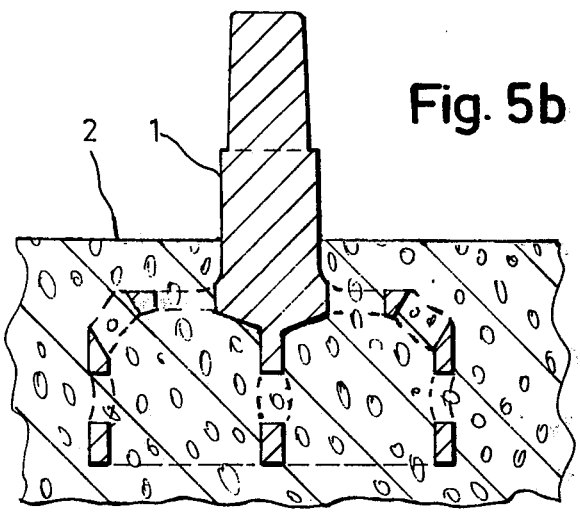
FIG. 5b shows a section similar to that of FIG. 5a, but at a later time when the bone has grown through the passages of the implant.

After the implants have been inserted, the alveolar bone 2 grows together again above the hollow cylinders as far as the post portions 1f, as shown in FIGS. 5b and 6. Furthermore, the blood vessels and bone will grow through the passages 1d. Therefore, the outer portions of bone and the studs of bone inside the hollow bodies 1a will join each other and the result will be a rigid and compact unit of bone and implant. As already indicated, the end walls 1c join the cylindrical walls 1b as well as the post 1e with rounded portions. This enables the bone to grow tightly over the end wall and also on the lower part of the post 1e. The rounded portions allow a direct contact between the bone and the titanium sprayed implant and prevent the formation of layers of connective tissue between said parts. Therefore, the rounded portions also avoid inflammations and bone resorption. Electron microscope investigations of implants, which had been inserted in the jaw of experimental animals, have shown that the bone also grows into the pores of the sprayed-on titanium layer. Since the implants 1 have a large area in contact with and growing together with the bone, even the pressure exerted upon the implants when bitting is uniformly distributed over a relatively large region of the bone. Therefore, although the implants are inserted to a sufficiently shallow depth not to extend as far as the nerve duct, they are very firmly anchored. In addition, the soft tissue portions 4 also grow up to the shafts 1e, resulting in a dense closure which prevents infections.

Figure 7:
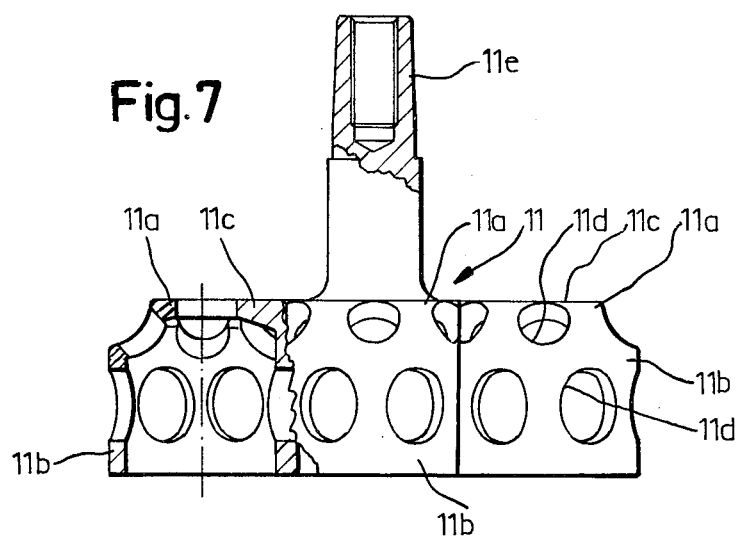
FIG. 7 shows an elevation corresponding to FIG. 1 of another implant comprising three hollow cylindrical bodies.
Figure 8:
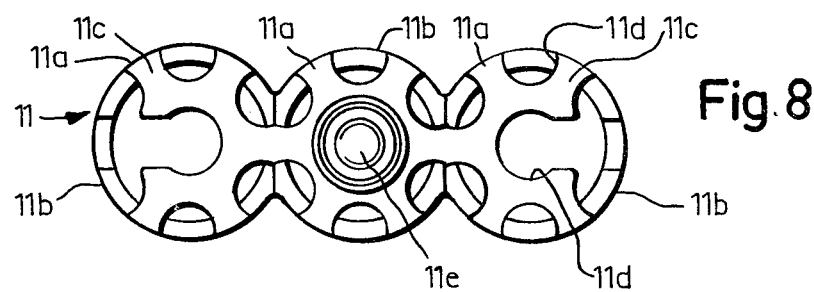
FIG. 8 shows a plan view of the implant shown in FIG. 7.

FIGS. 7 and 8 show an implant 11, which comprises three hollow cylindrical bodies 11a with mutually parallel axes lying in a common plane. The cylindrical walls 11b of the two outermost hollow bodies are integrally connected with that of the central hollow body. The hollow bodies 11a are closed at their upper end by end wall 11c. The post 11e is coaxial with the axis of the middle hollow body. The walls 11b, 11c are provided with through passages 11d, which are for the most part formed by bores. Between each bore situated at the centre of the end wall 11c of one of the two outer hollow bodies and the two bores adjacent to this bore and situated on the side of it remote from the other hollow bodies, there is a slit. This slit, together with the aforementioned three bores, therefore constitutes a common through passage, the transition regions of which may be somewhat rounded. The implant 11 can be inserted into a bone in a manner analogous to that of the implant 1, it being necessary for three annular grooves to be milled into the bone.

Figure 9:
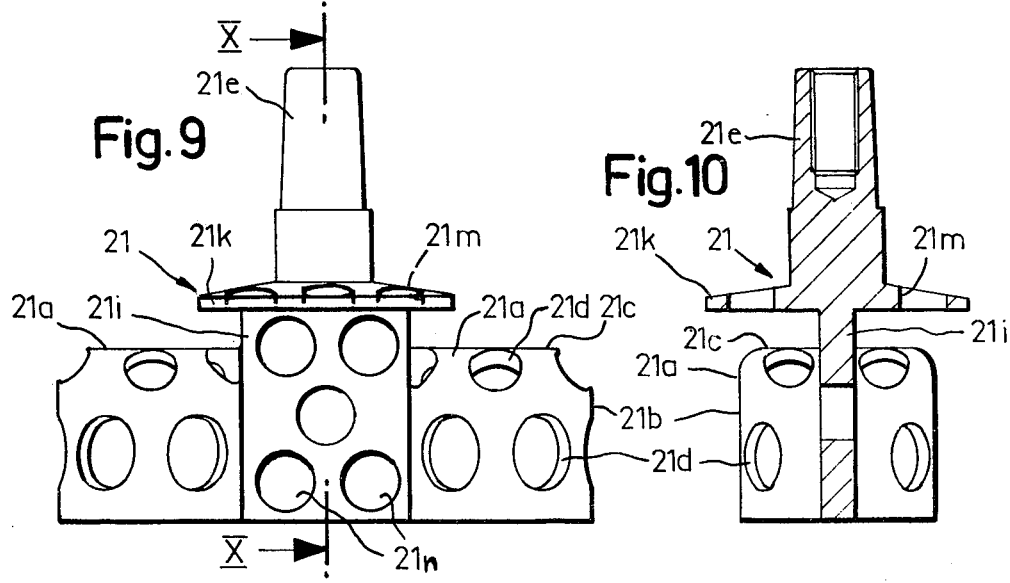
FIG. 9 shows an elevation corresponding to FIG. 1 of a further implant comprising two hollow cylindrical bodies joined together by a web and FIG. 10 shows a section along X—X of FIG. 9.
Figure 10:
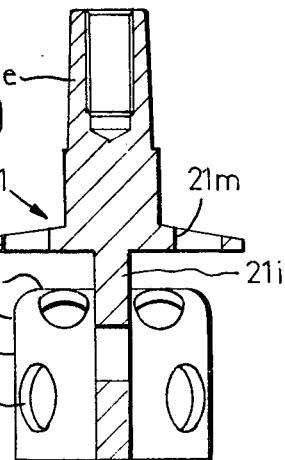

The implant 21 shown in FIGS. 9 and 10 comprises two hollow cylindrical bodies 21a each having a cylindrical wall 21b and an end wall 21c. The walls are provided with through bores 21d in a manner similar to those of the embodiments described above. However, the cylindrical walls 21b do not, in this embodiment join each other directly, but are integrally joined by a web 21i, which is bounded on its wide faces by flat surfaces extending parallel to the two axes of the hollow bodies. The web 21i extends over the entire length of the hollow bodies 21a and, at their upper closed ends, also projects somewhat above them. The web is also provided with passages 21n, which are formed by bores and are fairly uniformly distributed over the wide face of the web. At the upper end of the web 21i, there is a disc-shaped collar 21k, having a diameter somewhat exceeding that of the hollow bodies and provided around its perimeter with bores 21m. Above the collar 21k there is a post 21e. To insert the implant 21 into the jaw, two openings need to be milled in the bone to receive the hollow bodies 21a and a straight groove between them to receive the web 21i. Furthermore, a circular bearing surface may also be milled above the straight groove, onto which surface the flat, lower face of the collar 21k can rest.

The hollow bodies 11a and 21a may have approximately the same dimensions as were stated for the hollow bodies 1a. The passages in the hollow bodies and, in the last embodiment also in the web and collar, preferably have diameters or widths of 1 to 2.5 mm. Also, the passages should be so distributed in the hollow body walls that continuous webs of material remain between them both approximately parallel to the axes of the hollow bodies and also approximately transverse to these axes. Furthermore, the passages may be so distributed that the passages situated above one another are staggered from one another, i.e., their central axes do not lie in the same plane passing through the axis of the hollow cylinders. In an analogous manner, the passages 21n above one another in a web 21i, if present, should also be staggered relative to one another.

All the implants may, as described in relation to the first embodiment, be formed of a single integral workpiece, with the exeption of the sprayed-on titanium coating. It is however, also possible to make them of several components welded together.

In the embodiments shown, the axes of the posts and of the hollow cylinders lie in one common plane. In implants which are intended for use in a relatively sharply curved portion of the jaw, the axes could lie in a cylindrical surface. In the embodiments shown in the drawings, the post is situated in the central plane between the axes of the two outermost hollow cylinders. It would also be possible for the axis of the post to coincide with the axis of one of the two outermost hollow bodies. It is also possible for the posts, where they join the remainder of the implant, to have a constriction, into which the bone and gum can grow.

The replacement teeth may be fixed either permanently or detachably to the implants. In the latter case, they may be taken out for cleaning. It is also possible not only for bridges but also for other artificial groups of teeth, for example entire rows of teeth, to be used as replacement teeth. In this case, the replacement teeth may be fixed, for example, by means of four implants instead of only two.

We claim:

1. An implant for fixing an articial replacement tooth to a jaw, comprising a post for firmly holding said replacement tooth and at least two hollow cylindrical bodies having parallel axes, said bodies each being rigidly connected to said post, open at a respective one axial end and having a cylindrical wall which is intended to be inserted into the bone of said jaw and which is provided with means defining passages therethrough.

2. An implant as claimed in claim 1, wherein said bodies are so directly connected with each other that said walls form an external surface free of gaps between said bodies.

3. An implant as claimed in claim 1, wherein said bodies are connected together by a web which is provided with means defining passages therethrough and which has major surfaces extending parallel to said axes and to each other.

4. An implant as claimed in claim 1, wherein said post is rigidly connected by one end portion thereof to said bodies, an outwardly projecting collar being provided on said end portion.

5. An implant as claimed in claim 1, wherein said post has an axis extending generally in a plane disposed centrally between said axes.

6. An implant as claimed in claim 1, wherein each said body at its axial end thereof nearest said post is provided with an end wall provided with means defining passages therethrough.

7. An implant as claimed in claim 1 wherein each said body at its axial end thereof nearest said post is provided with an end wall, said end wall and said cylindrical wall being joined with a rounded portion.

8. An implant as claimed in claim 1, wherein said post joins the adjacent part with a rounded portion.

9. An implant as claimed in claim 1, wherein each said body has an external diameter which is from 0.75 to 1.25 times the axial length of said respective body.

10. An implant as claimed in claim 1 and of unitary metallic construction.

11. An implant as claimed in claim 1, comprising a basic member of non-porous metallic material, said body being provided at least on its outer surface with a coating of titanium containing pores.

12. An implant as claimed in claim 11, wherein said coating has been applied by flame spraying.

13. An implant as claimed in claim 11, wherein the basic member comprises titanium.

14. An implant for fixing an artificial replacement tooth to a jaw, comprising at least two hollow cylindrical body portions each having a cylindrical wall and abutting and joined to the other of said cylindrical walls, and having a first end wall at one end and an opposite end which is open, both said cylindrical side wall and said end wall having at least one passage therethrough, a post portion having an inner end joined to said body first wall and having an opposite outer free end means carried by said opposite outer free end for securing a replacement to said post portion.

15. An implant according to claim 14 wherein said at least two cylindrical body portions comprises first and second cylindrical bodies, said post portion being joined to said bodies at said first wall and at the juncture of said bodies.

16. An implant according to claim 14 wherein said at least two cylindrical bodies comprise three cylindrical body portions including a central body portion and an end body portion on each side of said central body portion and joined thereto, said post being centrally arranged in respect to said central body portion and joined to said central body portion first end wall.

17. An implant according to claim 1 including a web disposed between said hollow body portions joining said body portions together, said post being connected to said web.

* * * * *